(12) United States Patent
Jones

(10) Patent No.: US 9,095,400 B2
(45) Date of Patent: Aug. 4, 2015

(54) HYGIENE COVER

(75) Inventor: Robert Ewan Jones, Hawthorn East (AU)

(73) Assignee: Adventech Pty Limited (AU)

( * ) Notice: Subject to any disclaimer, the term of this patent is extended or adjusted under 35 U.S.C. 154(b) by 159 days.

(21) Appl. No.: 13/058,848

(22) PCT Filed: Jul. 21, 2009

(86) PCT No.: PCT/AU2009/000931
§ 371 (c)(1),
(2), (4) Date: Apr. 11, 2011

(87) PCT Pub. No.: WO2010/017574
PCT Pub. Date: Feb. 18, 2010

(65) Prior Publication Data
US 2011/0177470 A1 Jul. 21, 2011

(30) Foreign Application Priority Data
Aug. 13, 2008 (AU) ................. 2008904134

(51) Int. Cl.
*A61C 1/16* (2006.01)
*A61B 19/08* (2006.01)
*A61G 15/16* (2006.01)

(52) U.S. Cl.
CPC ................. *A61C 1/16* (2013.01); *A61B 19/081* (2013.10); *A61G 15/16* (2013.01)

(58) Field of Classification Search
CPC ........ A61B 19/081; A61C 1/16; A61G 15/16; B29C 51/10
USPC .......... 433/116; D24/176, 199, 128; 264/554; 362/400, 457, 804, 109, 285, 376, 399, 362/458
See application file for complete search history.

(56) References Cited

U.S. PATENT DOCUMENTS

| | | | | |
|---|---|---|---|---|
| 4,704,237 A * | 11/1987 | Taylor et al. | ................. | 264/40.1 |
| 4,880,381 A * | 11/1989 | Nieusma, Jr. | ................... | 433/28 |
| 5,128,090 A * | 7/1992 | Fujii et al. | ...................... | 264/511 |
| 5,332,392 A * | 7/1994 | Bierbaum et al. | .............. | 433/77 |
| 5,407,354 A | 4/1995 | Fife | | |
| 5,913,422 A | 6/1999 | Cote et al. | | |
| 2005/0181327 A1 | 8/2005 | Graham et al. | | |

FOREIGN PATENT DOCUMENTS

| WO | 9607364 | 3/1996 |
|---|---|---|
| WO | WO 9607364 A1 * | 3/1996 |
| WO | 9838943 | 9/1998 |

OTHER PUBLICATIONS

Univ. of Texas Arlington, Dept. of Kenesiology, KINE 3301 Biomechanics of Human Movement, Lesson 14 Mechanical Properties of Materials, http://wweb.uta.edu/faculty/ricard/Classes/KINE-3301/Notes/Lesson-14.html.*

* cited by examiner

*Primary Examiner* — Cris L Rodriguez
*Assistant Examiner* — Mirayda A Aponte
(74) *Attorney, Agent, or Firm* — Warner Norcross & Judd LLP

(57) ABSTRACT

A cover for a dental tool holder including a cover portion adapted for fitting over a receptacle of the tool holder so as to prevent direct contact between a dental tool and the dental tool holder when the tool is held within the holder.

9 Claims, 15 Drawing Sheets

HYGIENE COVER

FIELD OF THE INVENTION

This invention relates to a hygiene cover, and more particularly, but not exclusively, to a disposable hygiene cover for a dental or other medical tool holder.

BACKGROUND OF THE INVENTION

It is common for medical practitioners, particularly dentists, to use tools held in tool holders which are fixed to a support. In a common arrangement, there are a plurality of tools supplied by a single compressed air source for applying air and/or water to the mouth of a patient for drilling and cleaning of their teeth. Suction devices for applying suction to the mouth of a patient are also supported on a holder. The tools are held in a tool holder which extends from a structure of furniture such as, for example, an operating chair on which the patient is seated during treatment, or a mobile cart.

In at least some jurisdictions, to avoid cross-contamination, it is a requirement that dental tool holders are cleaned between treating patients (or that a physical barrier is placed between the tool and the holder). However, the applicant has identified that in many instances a dental practitioner may not adequately clean the tool holder, either through negligence or through the inability to adequately clean the intricate shaping of the tool holder, and may not place a physical barrier between the holder and the tool.

The present invention seeks to overcome or at least alleviate the problems discussed above.

SUMMARY OF THE INVENTION

In accordance with one aspect of the present invention, there is provided a cover for a tool holder including a cover portion adapted for fitting over a receptacle of the tool holder so as to prevent direct contact between a tool and the tool holder when the tool is held within the holder.

Preferably, the tool is a dental tool, and the tool holder is a dental tool holder.

Preferably, the cover is preformed with the same general shape as the tool holder so as to conform with a surface of the tool holder. More preferably, the cover is formed by a process of vacuum forming.

Preferably, the dental tool holder has a pair of claws with the receptacle formed between the claws, the claws are arranged to hold the dental tool in the receptacle, and the cover has a pair of correspondingly shaped sockets for fitting over the claws.

In a preferred form, the cover has a deformable portion to allow operation of a button/switch located in the receptacle by a body of the tool when the tool is moved into and removed from the tool holder. Other forms of holder may not have a button/switch, and for those kinds of holders it is not necessary to provide a deformable portion in the cover.

Preferably, the cover has at least one side aperture to allow access to a side hole of the tool holder required for fixing the tool holder to a support in the case of an individual/modular holder.

It is preferred that the cover fits as a sleeve over the holder, and has an opening to accommodate a tube which runs between the tool and a source of compressed air/power/suction.

In accordance with another aspect of the present invention, there is provided a medical tool holder having a medical tool held by the holder, and a removable cover fitted to the tool holder whereby the cover is interposed between the tool and the tool holder to prevent cross contamination between the tool and the tool holder.

In accordance with another aspect of the present invention, there is provided a method of forming a cover for a tool holder, including the steps of:
taking an impression of the tool holder;
forming a casting from the impression; and
vacuum forming a plastic material over the casting to form the cover.

Preferably, the tool holder is a dental tool holder

Preferably, the plastic material has a thickness between 0.1 mm and 1 mm. More preferably, the plastic material is double thickness polyethylene, with each thickness being 150 micron such that the total thickness of the plastic material is 300 microns.

In a preferred form, the material is Styrene (HIPS), PETG, or polyethylene. The polyethylene material may be supplied in the form of heat shrink wrap material.

In accordance with yet another aspect of the present invention, there is provided a method of using a cover for a tool holder, including the steps of:
fitting the cover over the tool holder;
placing a tool within a receptacle of the tool holder with the cover arranged to prevent contact between the tool and the tool holder;
using the tool to service a patient;
discarding the cover; and
fitting an unused cover over the tool holder for servicing another patient.

Preferably, the tool is a dental tool, and the tool holder is a dental tool holder.

BRIEF DESCRIPTION OF THE DRAWINGS

The invention is described, by way of non-limiting example only, with reference to the accompanying drawings in which.

DETAILED DESCRIPTION

Figure 1:
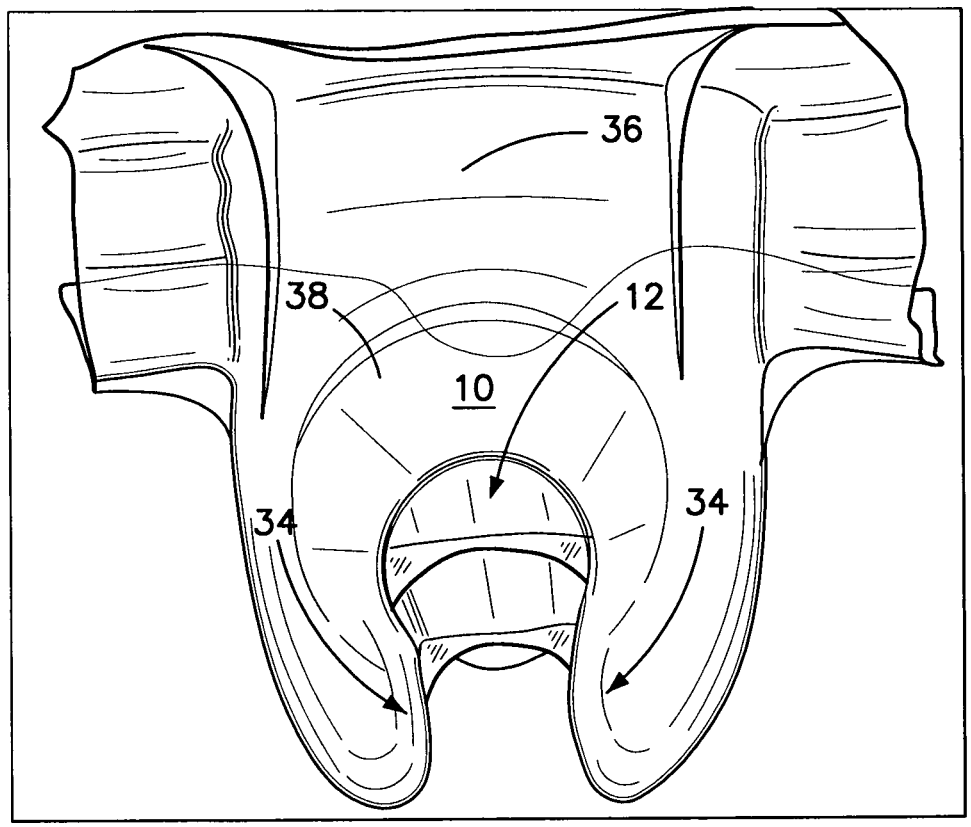
FIG. 1 is a top perspective view of a hygiene cover for a dental tool holder.
Figure 2:
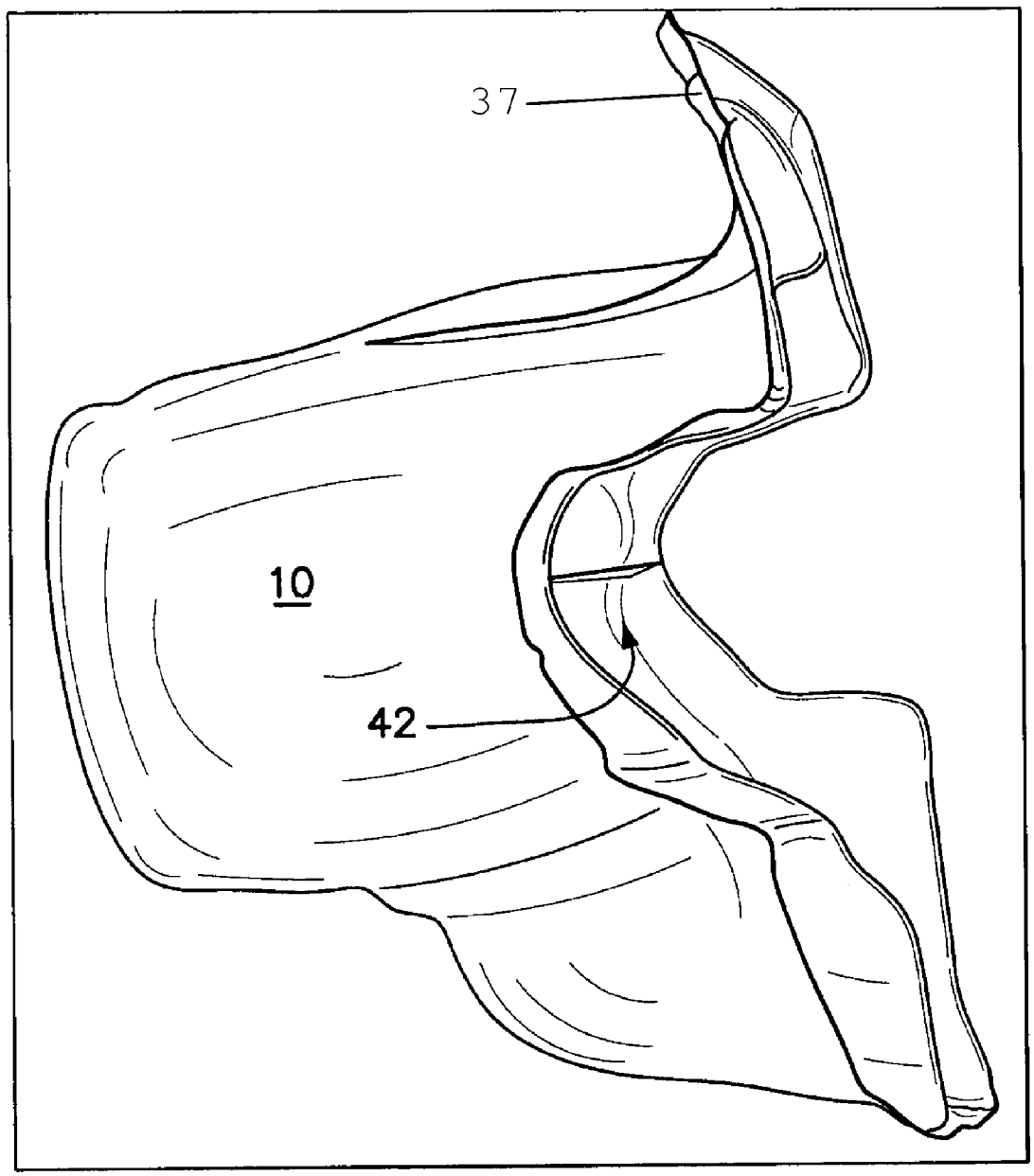
FIG. 2 is a side view of the hygiene cover shown in FIG. 1.
Figure 3:
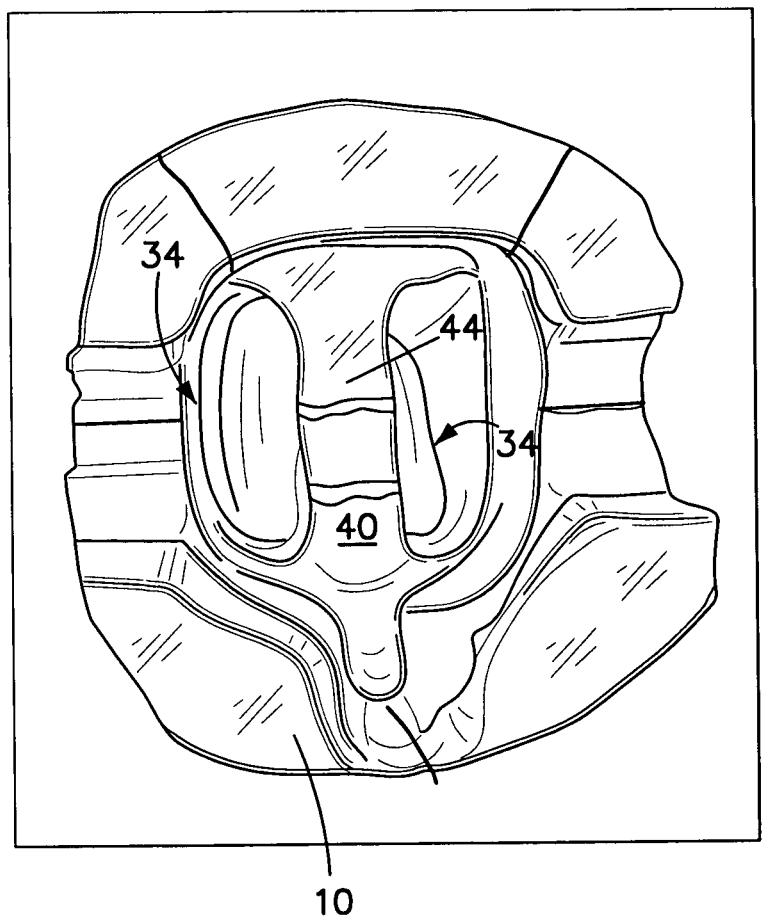
FIG. 3 is a rear view of the hygiene cover shown in FIGS. 1 and 2.
Figure 4:
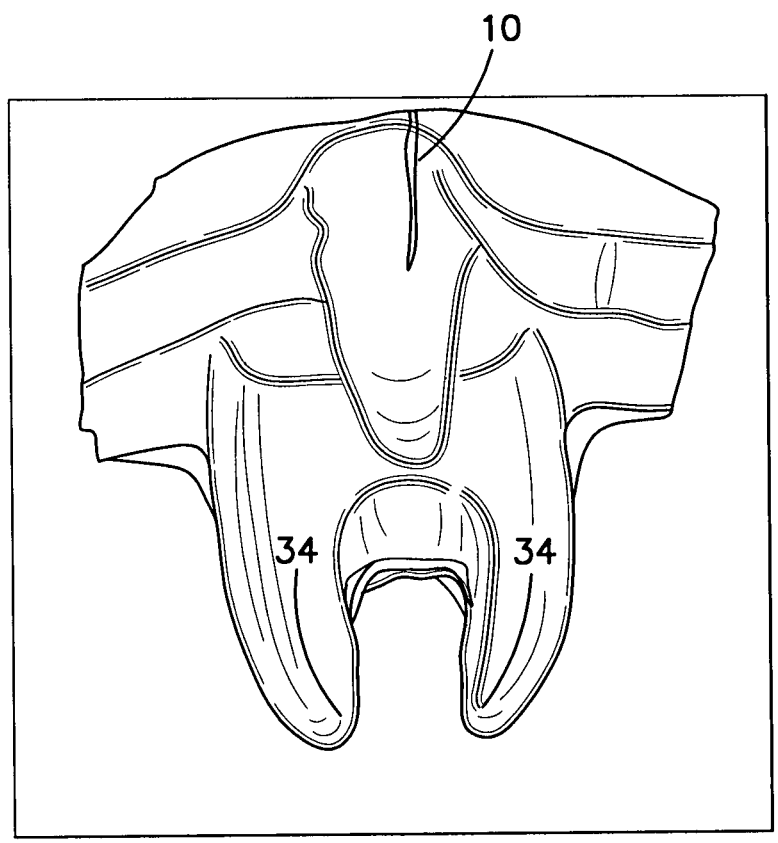
FIG. 4 is a bottom perspective view of the hygiene cover shown in FIGS. 1 to 3.

With reference to FIGS. 1 to 4, a hygiene cover 10 for a dental tool holder 12 in accordance with an example of the present invention includes a cover portion 14 adapted for fitting over a receptacle 16 of the tool holder 12 so as to prevent direct contact between a dental tool 18 and the dental tool holder 12 when the tool 18 is held within the holder 12. Accordingly, the hygiene cover 10 prevents cross contamination from the dental tool 18 to the dental tool holder 12, and thus also prevents cross contamination between patients provided the hygiene cover 10 is discarded and replaced between treating different patients.

Figure 5:
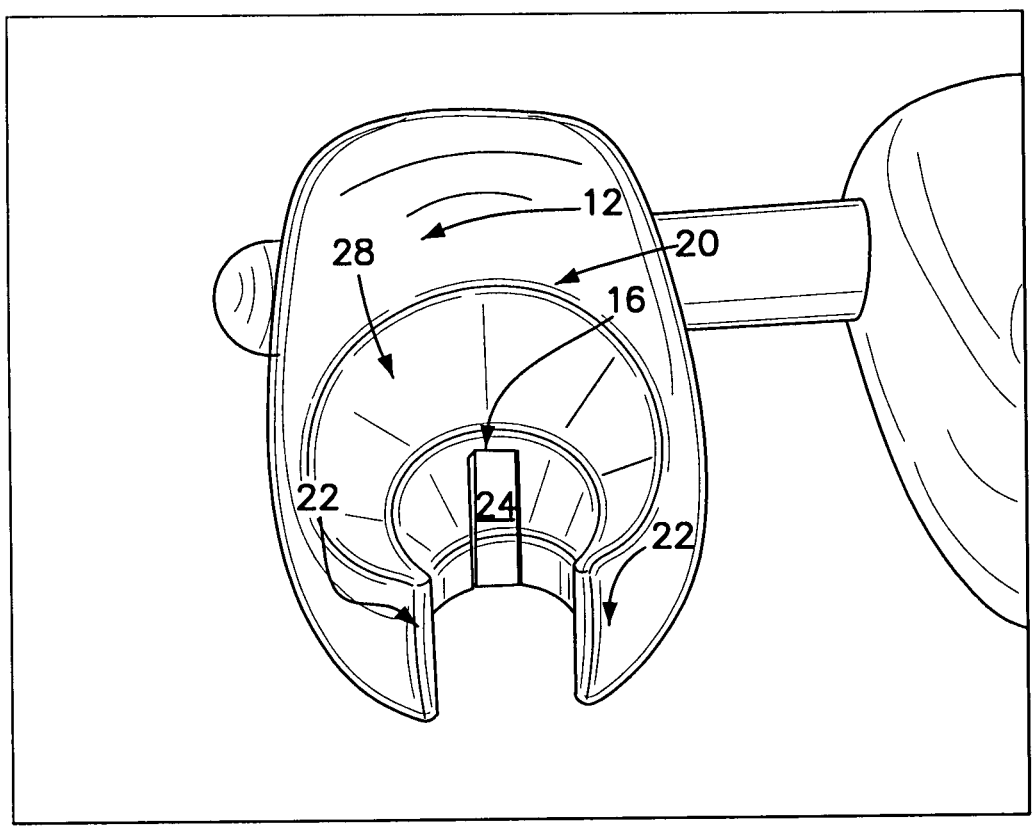
FIG. 5 is a top perspective view of a dental tool holder.
Figure 6:
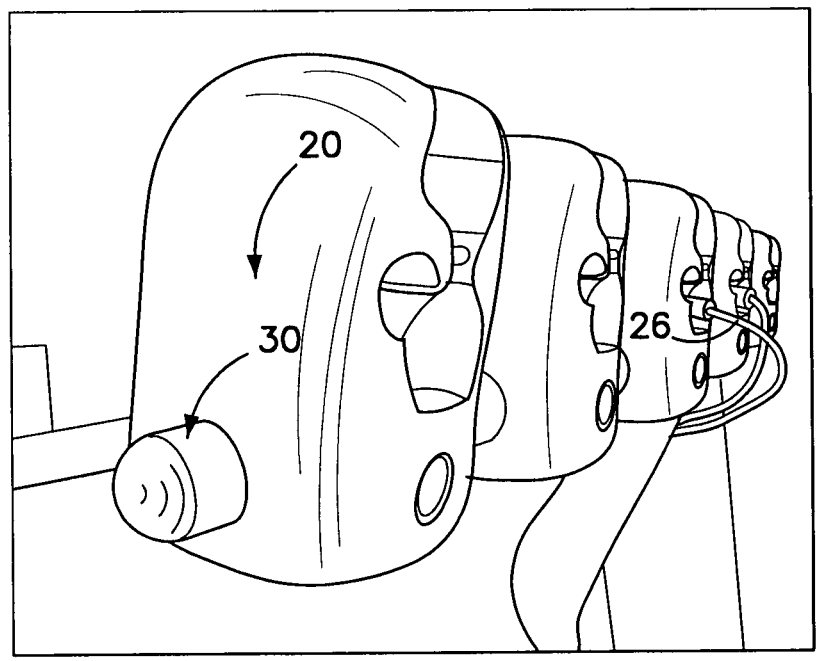
FIG. 6 is a side perspective view of the dental tool holder shown in FIG. 5.

FIGS. 5 and 6 show detail of a typical dental tool holder 12 which incorporates a holder body 20 having a pair of claws 22 with the receptacle 16 therebetween. The claws 22 extend around the receptacle 16 in a curved manner and are arranged to hold the dental tool 18 in the receptacle 16. A button/switch 24 is located in the receptacle and is actuated to signal the presence of the dental tool 18 in place in the dental tool holder 12 so that supply of air or electrical power from a compressed air/electrical power source to the dental tool 18 can be activated accordingly. Activation control to the dental tool is communicated from the dental tool holder 12 to the dental tool 18 via a tubular line 26 which, in examples, may exit the dental tool holder 12 at a rear end or underside of same. The holder body 20 is generally tubular, and has a curved cutaway 28 adjacent the receptacle 16 to facilitate insertion of the dental tool 18 into the receptacle 16.

Figure 12:
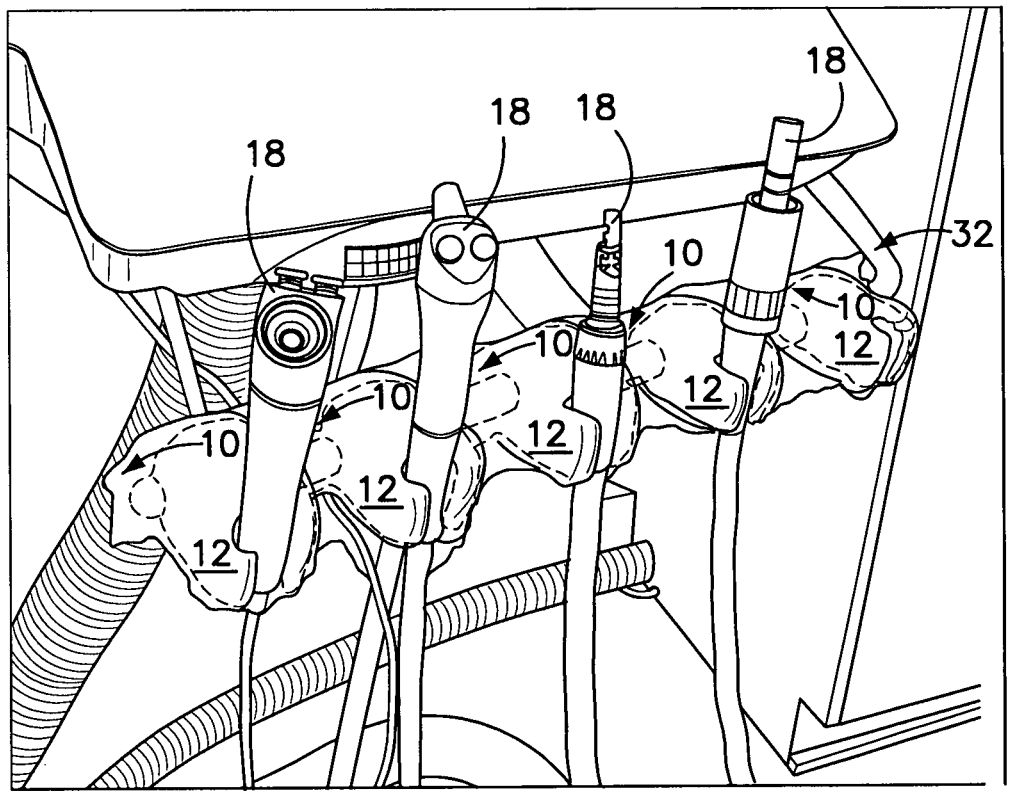
FIG. 12 is a perspective view of a plurality of dental tool holders, each fitted with a hygiene cover.

With reference to FIG. 6, the dental tool holder 12 is provided with a hole 30 which extends through the dental tool holder 12 in a direction perpendicular to an axis of the receptacle 16, so as to fix the dental tool holder 12 to a support 32 as shown in FIG. 12. Although the hygiene cover 10 shown in the drawings is adapted for use with the dental tool holder 12 shown in FIGS. 5 to 10 and 12, it will be appreciated by those skilled in the art that alternative examples of the invention may be formed for use with other types of dental tool holders (such as, for example, the unitary multiple tool holder shown in FIG. 13).

Figure 7:
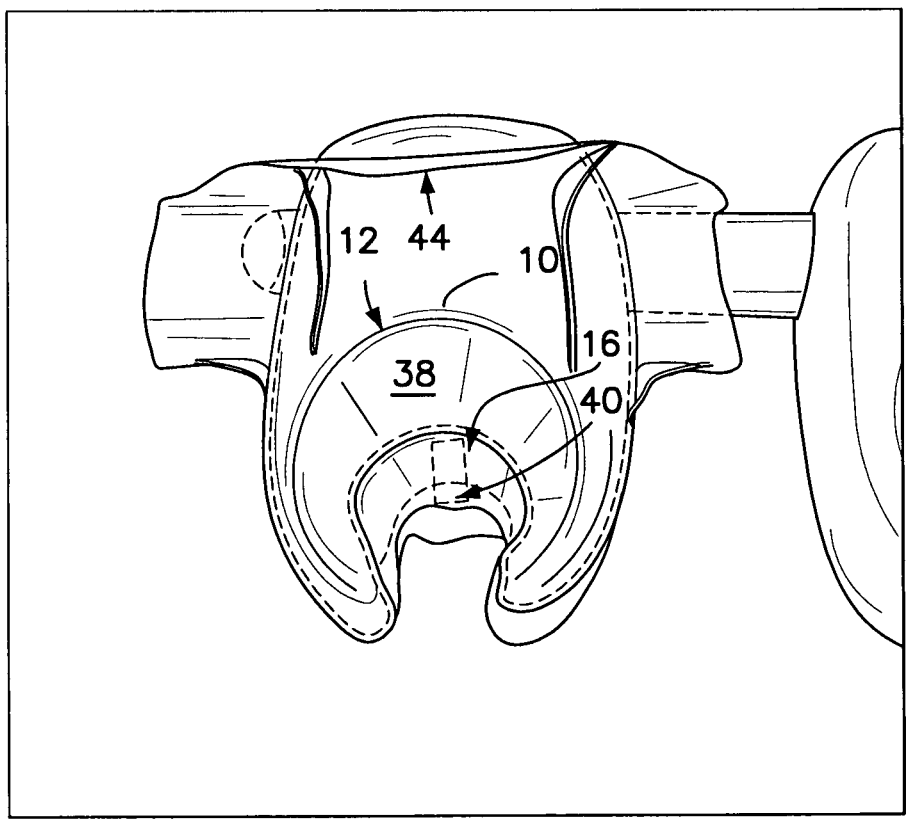
FIG. 7 is a top perspective view of the hygiene cover shown in FIGS. 1 to 4 fitted over the dental tool holder shown in FIGS. 5 and 6.
Figure 8:
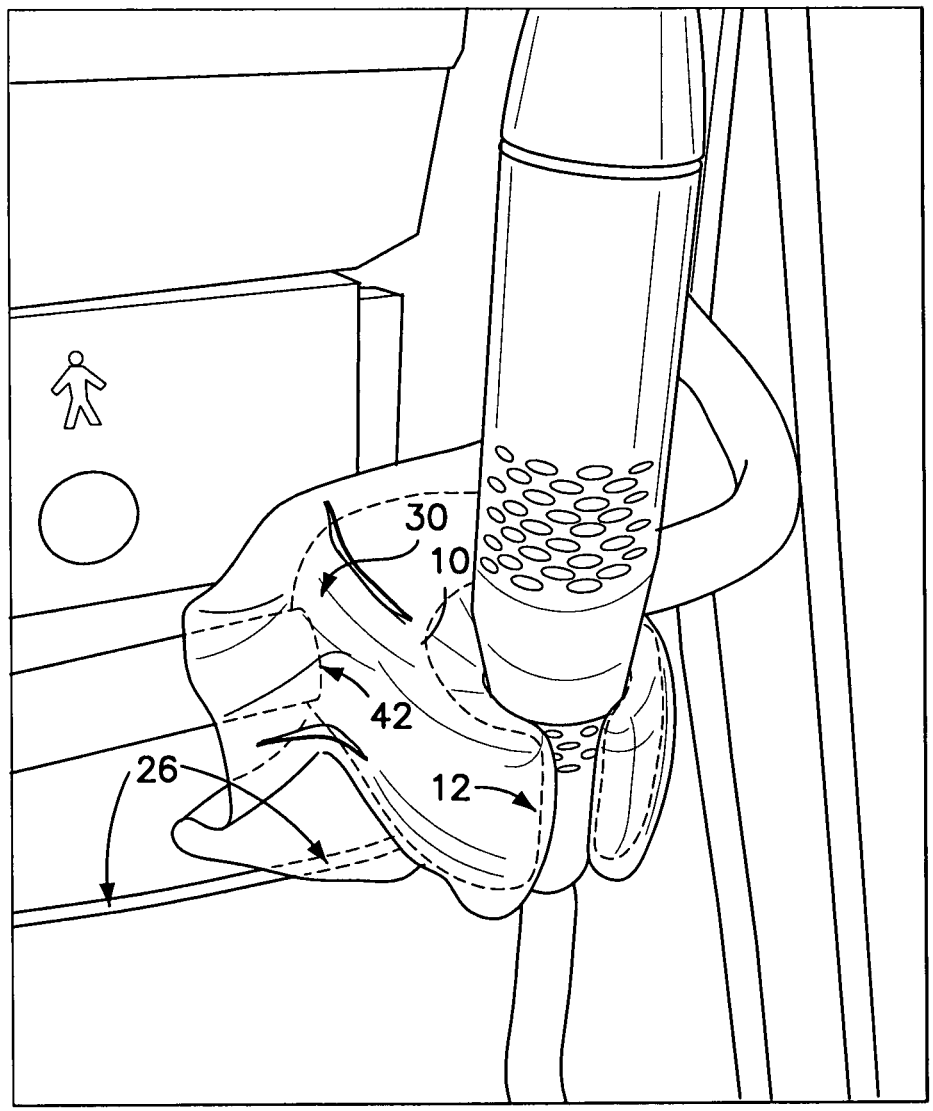
FIG. 8 is a side perspective view of the hygiene cover shown fitted over the dental tool holder, with a tool in place in the holder.
Figure 9:
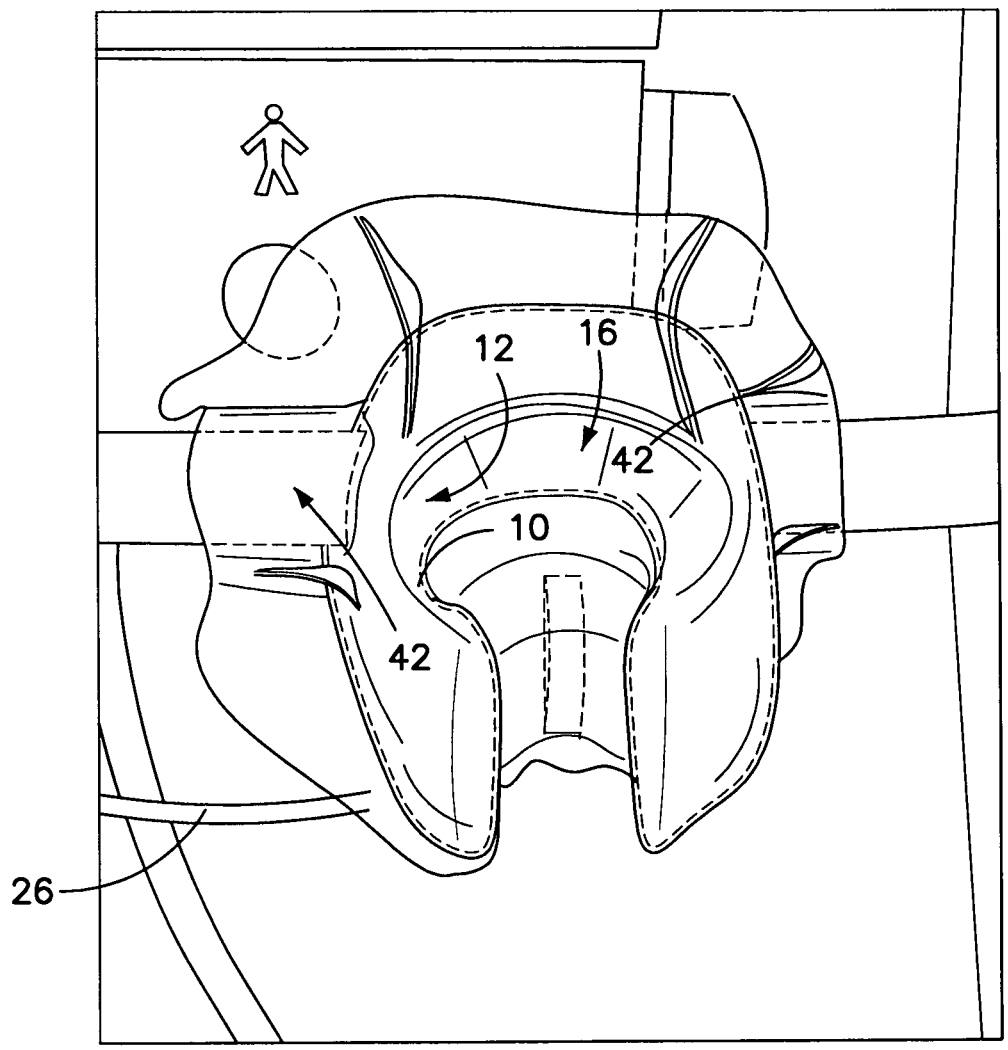
FIG. 9 is a front view of the hygiene cover shown fitted over the dental tool holder.
Figure 10:
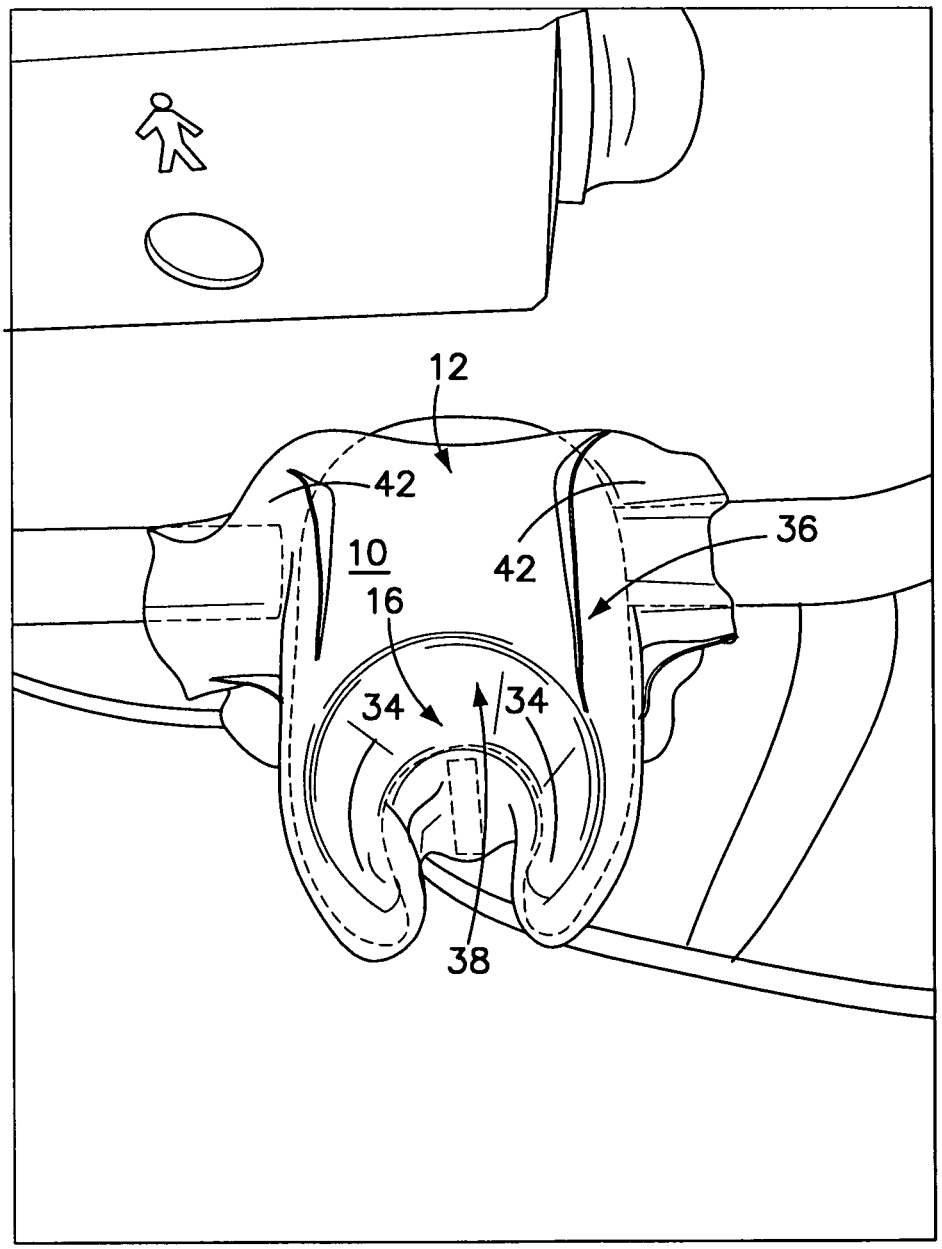
FIG. 10 is a top view of the hygiene cover shown fitted over the dental tool holder.

FIGS. 7 to 10 show various views of the hygiene cover 10 fitted in place over the dental tool holder 12. The cover 10 is preformed with the same general shape as the tool holder 12 so as to conform with a surface of the tool holder 12. More specifically, the cover 10 has a pair of sockets 34 which are correspondingly shaped so as to fit neatly over the claws 22, as shown in FIGS. 7 and 10. The hygiene cover 10 also has a tubular portion 36 to conform with the surface of the tubular holder body 20, as well as a cutaway portion 38 for conforming with the surface of the cutaway 28 of the tool holder 12. The rear of the hygiene cover 10 is formed into a protective collar 37 which further assists in preventing contamination of the tool holder 12.

To allow operation of the button 24 located in the receptacle 16 by a body of the dental tool 18 when the tool 18 is moved into and removed from the tool holder 12, a deformable portion 40 is provided at a location corresponding to the location of the button 24 on the tool holder 12. In this way, operation of the button 24 is not adversely affected by the presence of the hygiene cover 10, such that the button 24 is pressed in to cut off compressed air or electrical power (or suction in the case of a suction holder) to the dental tool 18 when the tool 18 is inserted in the receptacle 16, and is released when the tool 18 is removed from the receptacle 16 so as to provide activation to the tool 18.

The cover 10 has an aperture 42 at each side to allow access to the side hole 30 of the tool holder so that the support 32 to which the tool holder 12 is fixed does not interfere with sleeved fitment of the cover 10 on the holder 12. A sleeve opening 44 at a rear end of the cover 10 facilitates snug fitment of the cover 10 on the tool holder 12, and may also accommodate the activation tubular line 26 (if present) which communicates between the tool 18 and the tool holder 12.

The hygiene cover 10 may be formed to suit a particular dental tool holder 12 by taking an impression of the dental tool holder 12 by pressing the holder 12 into a material such as plasticine or the like, and by forming a casting (for example in plaster) from the impression. Plastic material is then vacuum formed over the casting to form the cover 10. The plastic material from which the hygiene cover 10 is made must be sufficiently thin to avoid obstruction of the receptacle 16 so that the dental tool 18 is still able to fit within the receptacle 16 with the cover 10 in place. Furthermore, the plastic material must allow deformation of the deformable portion 40 so as to facilitate operation of the button 24. The applicant has determined that the plastic material may be styrene (HIPS), PETG, or polyethylene. One form of polyethylene which has been found by the applicant to be particularly suitable is heat shrink-wrap, and the hygiene cover 10 shown in the drawings is formed of that material. In development conducted by the applicant to date it appears that heat shrink-wrap polyethylene has been the most successful of the materials tested so far, however it is possible that other materials not yet tested may also prove well-suited to use in forming the hygiene cover.

Figure 11:
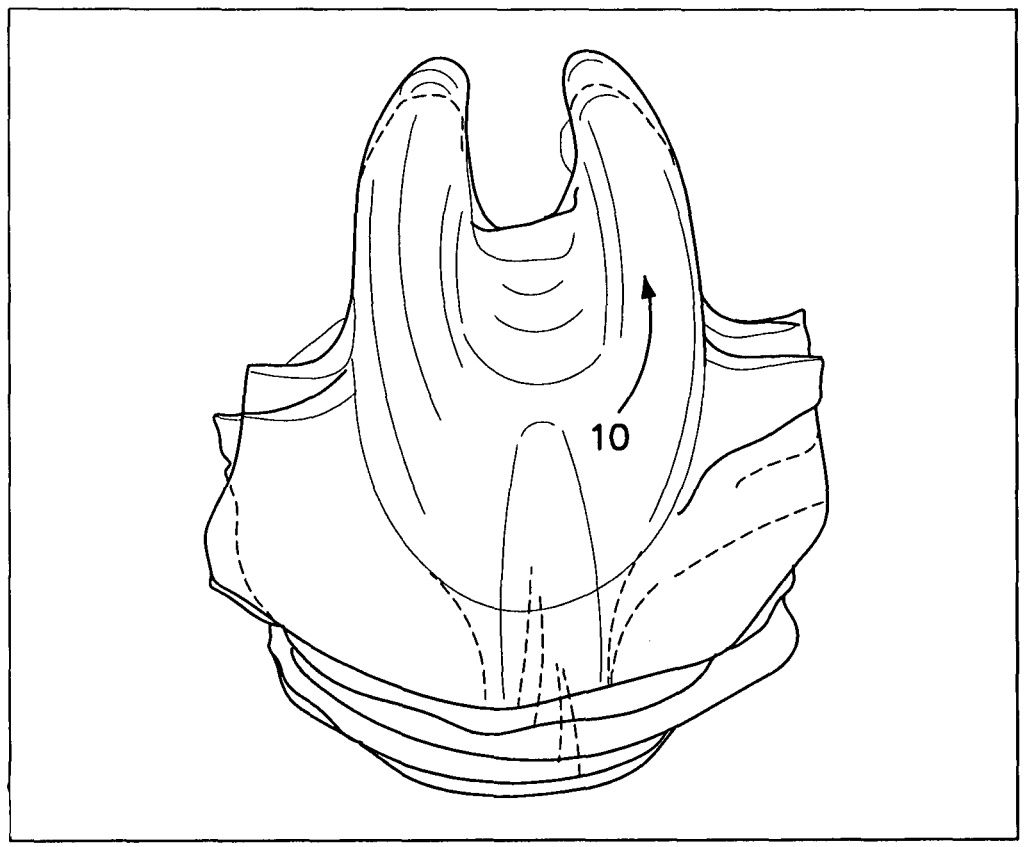
FIG. 11 is a perspective view of a plurality of like hygiene covers shown in a stacked configuration.

With regard to FIG. 11, the hygiene cover 10 is shaped to allow easy removal of the formed cover 10 from the casting, and to enable stacking of multiple like hygiene covers to facilitate storage of bulk quantities of the covers 10. This will allow for convenient purchase and storage of the covers 10 by dentists so that the covers can be discarded and replaced between treating different patients to avoid cross-contamination.

Figure 13:
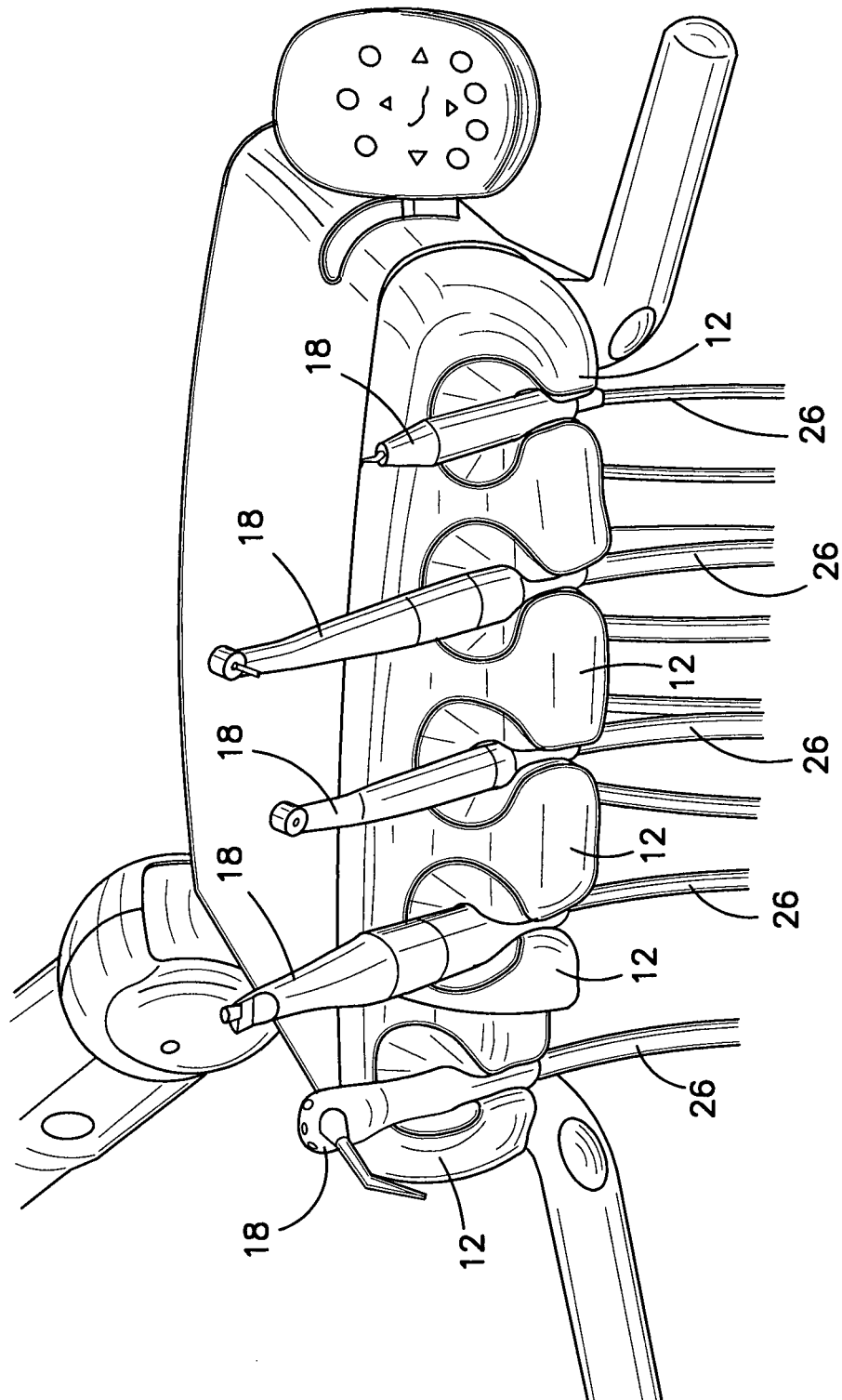
FIG. 13 is a front perspective view of a unitary dental fitting incorporating a plurality of dental tool holders.

With reference to FIGS. 12 and 13, it is typical for a plurality of dental tool holders 12 to be provided side-by-side, and although the covers 10 shown in FIG. 12 are shown as separate units, in an alternative example they may be formed in a single piece. Furthermore, although one particular form of dental tool holder 12 has been shown and described in detail, it will be appreciated that alternative examples of the present invention may provide covers suitable for other forms of tool holders, such as the unitary multiple tool holder shown in FIG. 13.

Figure 14A:
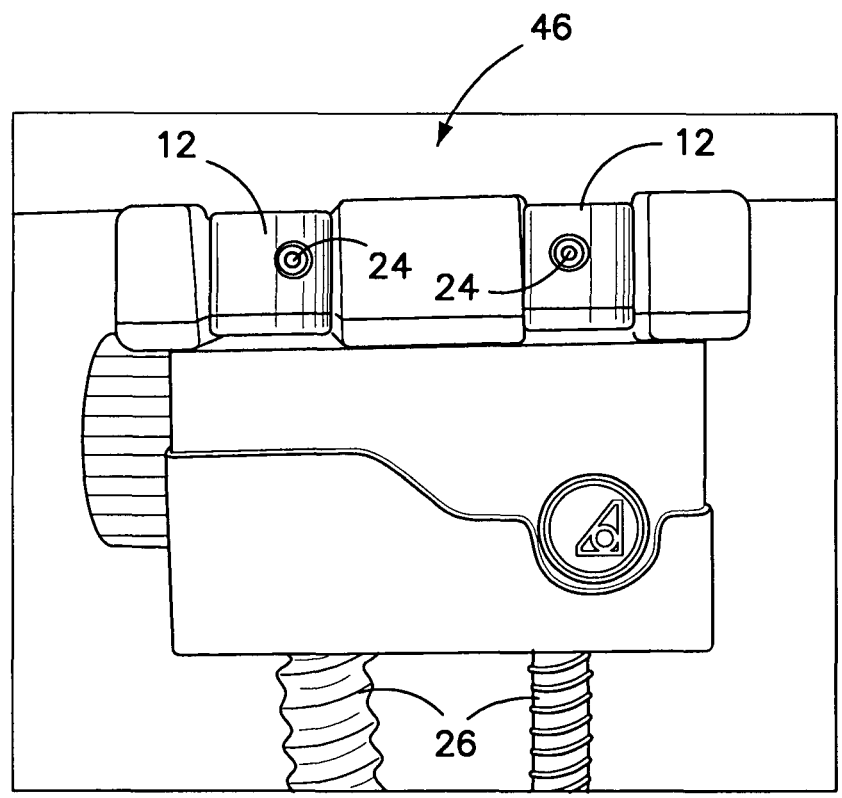
FIG. 14*a* is a front perspective view of a unitary dental fitting incorporating a plurality of dental suction holders.
Figure 14B:
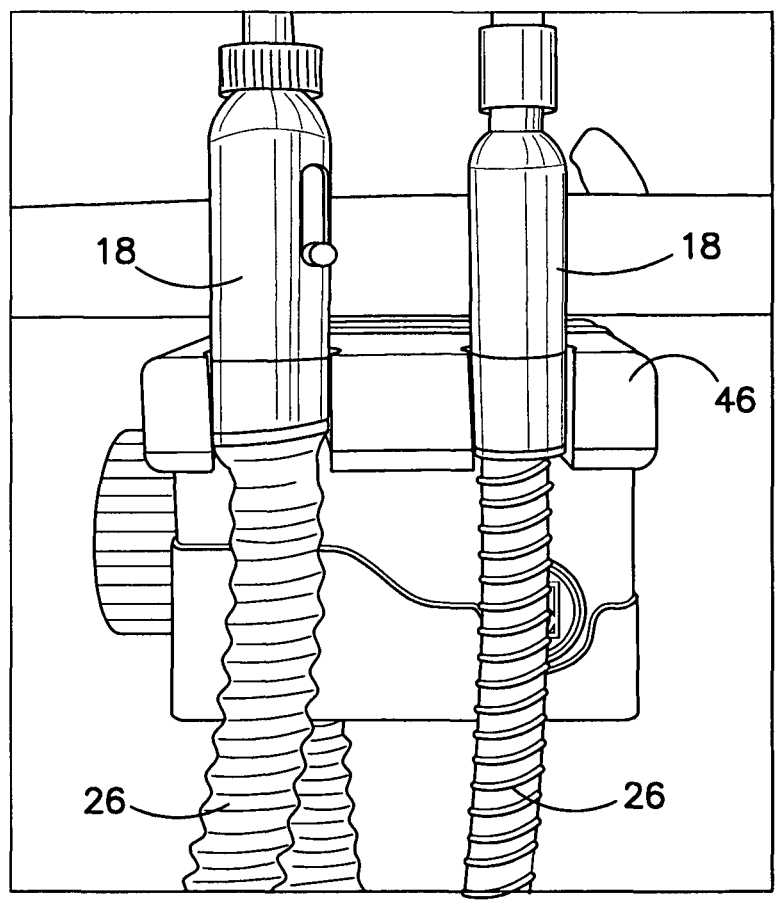
FIG. 14b is a front perspective view of the unitary dental fitting incorporating a plurality of dental suction holders, with a pair of suction tools in place in the holders.

FIGS. 14a and 14b show a unitary dental fitting 46 incorporating a plurality of dental suction holders, with a pair of suction tools in place in the holders. The unitary dental fitting 46 has features in common with the holders shown in the previous Figures, and like features are referenced by like reference numerals. The unitary dental fitting 46 shown in FIGS. 14a and 14b has a depressable button/switch in the receptacle to signal the presence or absence of the dental suction tool in the suction holder to provide activation control of the dental suction tools 18 by supplying suction (in contrast to the supply of compressed air and/or electrical power in the previous examples). The unitary dental fitting 46 drawn in FIGS. 14a and 14b does differ in that there is no activation tubular line 26. The general principle of using the hygiene covers 10 to form a barrier between the tools 18 and the holders 12 is however the same.

The above-described hygiene cover 10 advantageously enables a user to conveniently avoid cross-contamination between patients. As the cover 10 prevents direct contact between the dental tool 18 and the dental tool holder 12 when the tool 18 is held within the holder 12, cross-contamination between the tool 18 and the holder 12 is prevented to obviate or reduce the need to clean the holder 12 between treating patients, and instead it is possible to simply discard the contaminated cover 10 and replace it with an unused cover 10 for servicing another patient.

While an example of the present invention has been described above, it should be understood that it has been presented by way of example only, and not by way of limitation. It will be apparent to a person skilled in the relevant art that various changes in form and detail can be made therein without departing from the spirit and scope of the invention. Thus, the present invention should not be limited by the above described examples. In particular, it will be appreciated by those skilled in the art that examples of the present invention may apply to tools and tool holders generally, and that such examples may be used beyond applications in the medical and dental fields.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The claims defining the invention are as follows:

1. A disposable cover for a dental tool hanger, the dental tool hanger including a pair of claws and a receptacle formed by the claws, the receptacle being configured to hold the dental tool in the receptacle, the disposable cover comprising:
    a pair of sockets adapted for neatly fitting to the claws of the tool hanger so as to prevent direct contact between the claws and the dental tool held within the dental tool hanger;
    wherein each socket is arranged to be slid rearwardly over a respective one of the claws into sleeved relationship in which a top shielding surface of the socket shields a top part of the claw, an inner shielding surface of the socket shields an inner part of the claw, a bottom shielding surface of the socket shields an underside of the claw and a front shielding surface of the socket shields a front part of the claw, and
    wherein the sockets are conformed to the shape of the claws and the receptacle of the tool hanger when fitted on the tool hanger such that the sockets achieve snug fitment on the tool hanger upon initial placement of the sockets into sleeved relationship on the claws of the tool hanger, and such that the shielding surfaces of the sockets do not substantially differ from the shape of the underlying tool hanger to enable the underlying tool hanger to hold the tool with the sockets in place over the claws.

2. A cover for a tool hanger as claimed in claim 1, wherein the cover is formed as a unitary structure formed of elastically deformable material.

3. A disposable cover for a tool hanger as claimed in claim 1, wherein the cover is formed by a process of vacuum forming.

4. A disposable cover for a tool hanger as claimed in claim 1, wherein the cover has a deformable portion to allow operation of a button/switch located in the receptacle by a body of the tool when the tool is moved into and removed from the tool hanger.

5. A disposable cover for a tool hanger as claimed in claim 1, wherein the cover has at least one side aperture to allow access to a side hole of the tool hanger required for fixing the tool hanger to a support.

6. A disposable cover for a tool hanger as claimed in claim 1, wherein the cover has an opening to accommodate an activation tube which runs between the tool and a source of compressed air, electrical power and/or suction.

7. A disposable cover for a tool hanger as claimed in claim 1, wherein the cover includes a protective collar formed at the rear end of the disposable cover for shielding the dental tool hanger.

8. A dental tool hanger having a dental tool held by the hanger, and a removable disposable cover fitted to the tool hanger whereby the cover is interposed between the tool and the tool hanger to prevent cross contamination between the tool and the tool hanger, and wherein the disposable cover is a cover as claimed in claim 1.

9. A method of using a disposable cover for a dental tool hanger, the dental tool hanger comprising a pair of claws and a receptacle formed by the claws, the receptacle being configured to hold a dental tool in the receptacle, including the steps of:
    manufacturing in resilient plastic material a plurality of interchangeable preformed identical disposable covers specifically formed to conform to a particular shape of the dental tool hanger, each of the covers being a cover as claimed in claim 1;
    sliding a first one of the covers rearwardly relative to the dental tool hanger such that each of the sockets of the cover are brought into sleeved arrangement with a respective claw of the dental tool hanger, wherein, for each socket, the top shielding surface of the socket shields a top part of the claw, the inner shielding surface of the socket shields an inner part of the claw, the bottom shielding surface of the socket shields an underside of the claw and the front shielding surface of the socket shields a front part of the claw;
    placing a tool within a receptacle of the dental tool hanger with the first cover arranged to prevent contact between the tool and the dental tool hanger;
    using the tool to service a patient;
    discarding the first cover; and
    fitting an unused second one of the covers over the dental tool hanger for servicing another patient.

* * * * *